(12) United States Patent
Lin et al.

(10) Patent No.: US 8,530,481 B2
(45) Date of Patent: *Sep. 10, 2013

(54) STABLE PHARMACEUTICAL COMPOSITION OF FREEZE-DRIED TETRODOTOXIN POWDER

(75) Inventors: Weiyang Lin, Kwaichung (HK); Xiaoyan Huang, Nanning (CN); Xiao Zhang, Nanning (CN)

(73) Assignee: Wex Medical Limited, Wanchai (HK)

( * ) Notice: Subject to any disclaimer, the term of this patent is extended or adjusted under 35 U.S.C. 154(b) by 0 days.

This patent is subject to a terminal disclaimer.

(21) Appl. No.: 13/533,907

(22) Filed: Jun. 26, 2012

(65) Prior Publication Data

US 2012/0264767 A1 Oct. 18, 2012

Related U.S. Application Data

(63) Continuation of application No. 12/650,864, filed on Dec. 31, 2009, now Pat. No. 8,222,258, which is a continuation of application No. 10/890,279, filed on Jul. 14, 2004, now Pat. No. 8,124,608.

(30) Foreign Application Priority Data

Jul. 14, 2003 (CN) .................................. 03146020

(51) Int. Cl.
*A61K 31/519* (2006.01)
*A61P 25/00* (2006.01)
*A61P 21/00* (2006.01)

(52) U.S. Cl.
USPC .......................................... 514/257; 424/489

(58) Field of Classification Search
USPC .......................................... 424/489; 514/257
See application file for complete search history.

(56) References Cited

U.S. PATENT DOCUMENTS

| | | | |
|---|---|---|---|
| 2,912,361 | A | 11/1959 | Froelich |
| 4,565,651 | A | 1/1986 | Ohmura et al. |
| 4,816,568 | A | 3/1989 | Hamilton, Jr. et al. |
| 5,846,975 | A | 12/1998 | Pan et al. |
| 5,977,172 | A | 11/1999 | Yoshikawa et al. |
| 6,030,974 | A | 2/2000 | Schwartz et al. |
| 6,166,062 | A | 12/2000 | Confer et al. |
| 6,407,088 | B1 | 6/2002 | Dong et al. |
| 6,478,966 | B2 | 11/2002 | Zhou et al. |
| 6,552,191 | B1 | 4/2003 | Zhou et al. |
| 6,559,154 | B2 | 5/2003 | Kang et al. |
| 6,562,968 | B2 | 5/2003 | Zhou et al. |
| 6,599,906 | B1 | 7/2003 | Ku et al. |
| 6,780,866 | B2 | 8/2004 | Ku et al. |
| 8,124,608 | B2 * | 2/2012 | Zhang et al. ............ 514/257 |
| 8,222,258 | B2 * | 7/2012 | Lin et al. ............ 514/257 |
| 2005/0020610 | A1 | 1/2005 | Zhang et al. |
| 2009/0105197 | A1 | 4/2009 | Ku et al. |

FOREIGN PATENT DOCUMENTS

| | | |
|---|---|---|
| CN | 1145225 | 3/1997 |
| JP | 9-136836 | 5/1997 |
| WO | WO93/00807 | 1/1993 |
| WO | WO95/24903 | 9/1995 |
| WO | WO98/51290 | 11/1998 |
| WO | WO01/93827 | 12/2001 |
| WO | WO02/22129 | 3/2002 |
| WO | WO03/099301 | 12/2003 |
| WO | WO2006/032459 | 3/2006 |
| WO | WO2006/032481 | 3/2006 |
| WO | WO2006/083840 | 8/2006 |
| WO | WO2007/025212 | 3/2007 |
| WO | WO2007/110221 | 10/2007 |

OTHER PUBLICATIONS

Bedu-Addo, F. K., "Understanding Lyophilization Formulation Development," *Pharmaceutical Technology—Lyophilization 2004*, pp. 10-18 (2004).
Born et al., "Afferent Influences on Brain Stem Auditory Nuclei of the chicken: Presynaptic Action potentials Regulate Protein Synthesis in Nucleus Magnocellularis Neurons", *The Journal of Neuroscience*, Mar. 1988, 8 (3): 901-919.
Goto et al., "Tetrodotoxin$^{1,2}$", *Tetrahedron*, vol. 21, (1965) pp. 2059-2088.
Griebenow et al., "Lyophilization-induced Reversible Changes in the Secondary Structure of Proteins," *Proc. Natl. Acad. Sci. USA*; vol. 92, pp. 10969-10976, Nov. 1995.
Indian Patent Office, Examination Report for Application No. 5833/DELNP/2005, dated Sep. 14, 2010, 2 pages.
Macarak et al., "Synthesis of Cold-insoluble Globulin by Cultured Calf Endothelial Cells," *Proc. Natl. Acad. Sci. USA*, vol. 75, No. 6, pp. 2621-2625, Jun. 1978.
Miyazawa et al., "Distribution and Origin of Tetrodotoxin," *J. Toxicol.—Toxin Reviews*, 20(1), pp. 11-33 (2001).
Mosher, H. S., "The Chemistry of Tetrodotoxin", *Annals New York Academy of Sciences*, vol. 479 (1985) pp. 32-43.
Nakamura, M. et al., "Tetrodotoxin Derivatives in Puffer Fish", *Toxicon*, vol. 23, No. 2, (1985) pp. 271-276.
Oglesbee et al., "Isolation and Characterization of Canine Distemper Virus Nucleocapsid Variants," *J. Gen. Virol.* 70, pp. 2409-2419, (1989).
Sigma-Aldrich website; T5651—Tetrodotoxin, <URL: http://www.sigmaaldrich.com/catalog/ProductDetail.do?lang=en&N4=T5651|SIGMA&N5=SEARCH_CONCAT_PNO|BRAND_KEY&F=SPEC, [retrieved on Mar. 5, 2009].
Sigma-Aldrich website; Terms & Conditions of Sale, <URL: http://www.sigmaaldrich.com/customer-service/policies.printerview.html, [retrieved on Dec. 31, 2009].
Sigma Alrdich, Tetrodotoxin with Citrate Buffer, Material Safety Data Sheet (6 pages) (2009).
Ting Guo (Authorized Officer), International Preliminary Report on Patentability of International Application No. PCT/2004/000736, dated Nov. 7, 2005, 4 pages.
Translation of Japanese Office Action, application No. JP 2006-519747 dated Dec. 17, 2010, 8 pgs.
Yotsu-Yamashita, "Chemistry of Puffer Fish Toxin," *J. Toxicol.—Toxin Reviews*, 20(1), 51-66 (2001).

* cited by examiner

*Primary Examiner* — Aradhana Sasan
(74) *Attorney, Agent, or Firm* — Fish & Richardson P.C.

(57) ABSTRACT

This invention relates to a stable pharmaceutical composition of freeze-dried tetrodotoxin powder which contains trace amount of tetrodotoxin, substances which can stabilizes tetrodotoxin, including disaccharide(s) or polyglucose(s) or analogues thereof and solvent(s), and solvents which can help tetrodotoxin dissolve.

49 Claims, No Drawings

STABLE PHARMACEUTICAL COMPOSITION OF FREEZE-DRIED TETRODOTOXIN POWDER

CROSS-REFERENCE TO RELATED APPLICATIONS

This application is a continuation of U.S. application Ser. No. 12/650,864 filed Dec. 31, 2009, which is pending, which is a continuation of U.S. application Ser. No. 10/890,279, filed Jul. 14, 2004, now U.S. Pat. No. 8,124,608, which claims the benefit of priority of Chinese Patent Application No. 03146020.8, filed Jul. 14, 2003. The entire disclosure of each of these related applications is hereby incorporated herein by reference.

FIELD OF THE INVENTION

This invention relates to a pharmaceutical freeze-dried composition, particularly freeze-dried tetrodotoxin powder safe for use in humans by injection.

BACKGROUND OF THE INVENTION

Being a naturally-occurring non-protein nervous toxin, tetrodotoxin binds with the SS1/SS2 subunit of sodium channels with high specificity and high affinity, and has been widely used as a tool drug in pharmacological research, particularly neuropharmacology and muscular physiology for decades. On the market, Sigma-Aldrich supplies a typical product of tetrodotoxin, a freeze-dried solid powder containing 1 mg of tetrodotoxin (product number T5881). In addition to its use in scientific research, therapeutic applications were discovered; among them a tetrodotoxin composition for injection (aqueous solution), intended for treatment of drug addiction and pain has been described (US patent Pan, et al. U.S. Pat. No. 5,846,975; Dong, et al. U.S. Pat. No. 6,407,088). However, tetrodotoxin injection (aqueous solution) is so sensitive to temperature that it degrades under temperature's influence; the higher temperature, the faster it degrades. Once the content of tetrodotoxin, the active pharmaceutical ingredient, is reduced to less than 90% of the labeled amount, or the relative content of related substances exceeds the specified limit by clinical standards (greater than the main peak area of a control solution), the drug will not be suitable for clinical use any more.

The chemical name of tetrodotoxin is octahydro-12-(hydroxymethyl)-2-imino-5, 9:7, 10a-dimethano-10aH-(1,3)dioxocino (6,5-d)-pyrimidine-4,7,10,11,12-pentol, with molecular formula $C_{11}H_{17}N_3O_8$ and molecular weight 319.28, which has the following structure:

Structure of Tetradotoxin

Tetrodotoxin darkens above 220° C. without decomposition. $[\alpha]_D^{25}$ -8.64 (C=8.55 in diluted acetic acid), pKa 8.76 (aqueous); 9.4 (50% alcohol). Soluble in diluted acetic acid, insoluble in water, dry alcohol, ether, insoluble in other organic solvents. Toxin is destroyed in strong acids and in alkaline solvents (The Merck Index. 13th Ed. 2001, 9318).

Tetrodotoxin in the solid state is relatively stable to heat, but not so when in aqueous solution, particularly in diluted acid aqueous solution with a low concentration (Kang, et al. U.S. Pat. No. 6,559,154).

DETAILED DESCRIPTION OF THE INVENTION

The inventors examined the tetrodotoxin injection solution for the content of tetrodotoxin and the relative content of related substances by HPLC, and discovered that the content of tetrodotoxin changed with temperature and duration of storage. The results suggest that the content of tetrodotoxin declined to 91.9% (dropped by 8.1%) on day 1 and further to 89.37% on day 3 at 40° C., a total drop of 10.63% (See Table 1), suggesting that the tetrodotoxin injection will fail to meet the clinical criteria after prolonged storage as its content will decline to less than specified limit after being exposed to 40° C. for three days. Moreover, the content of tetrodotoxin declined to 95.34% after the injection had been standing for one month at 25° C., whereas the related substances had a relative content greater than the main peak area of the control solution, exceeding the specified limit and not meeting the clinical criteria. After standing for three months, the content of tetrodotoxin declined to 89.77%, a drop of 10.23%, while the related substances had a relative content greater than the main peak of the control solution, thus neither met the clinical criteria (See Table 2). These results indicate that the quality of tetrodotoxin injection is not accountable at 25° C., and the content of related substances exceeds the specified limit after one month, not meeting the clinical criteria. To ensure the quality and prevent the content of tetrodotoxin from declining and the content of related substances from escalating, tetrodotoxin injection must be stored in a refrigerator at the range of 4-8° C. Such requirement makes its clinical use difficult and inconvenient as the temperature must be kept at 4-8° C. at all relevant occasions including storage, transportation, loading and unloading, wholesale and retail, hospital and administration, otherwise higher temperature can be detrimental to the clinical effect. Therefore, it is necessary to solve this problem by developing a safe and stable product which can be stored at room temperature.

TABLE 1

Stability Study on Tetrodotoxin Injection (990120A) at 40° C.

| Conditions | Duration of Storage | Appearance | Content (%) | Remarks |
| --- | --- | --- | --- | --- |
| 40° C. | Day 0 | Colorless, transparent liquid | 100 | Content at |
| | Day 1 | Colorless, transparent liquid | 91.9 | day 0 is |
| | Day 3 | Colorless, transparent liquid | 89.37 | set to |
| | Day 5 | Colorless, transparent liquid | 87.45 | be 100%. |
| | Day 10 | Colorless, transparent liquid | 88.06 | |

Note:
The criteria are not met when the content of tetrodotoxin is less than 90%.

TABLE 2

Stability Study on Tetrodotoxin Injection at 25° C.

| Duration of Storage (months) | Content (%) | Related substances (%) | Remarks |
|---|---|---|---|
| 0 | 100 | <main peak area of control solution | Content at day 0 is set to be 100%. |
| 1 | 95.34 | >main peak area of control solution | |
| 2 | 93.72 | >main peak area of control solution | |
| 3 | 89.77 | >main peak area of control solution | |
| 6 | 82.47 | >main peak area of control solution | |

Note:
The criteria are not met if content of tetrodotoxin is less than 90% or the related substances' content is greater than the main peak of control solution.

The studies show that tetrodotoxin injection (liquid form) is not stable at room temperature, entailing storage at low temperatures at 4-8° C., thus making it inconvenient to transport and store. A simple solution for this problem appears to be a freeze-dried powder formulation of tetrodotoxin. A bioactive substance that is unstable in aqueous solution can have often its storage duration prolonged by way of freeze-drying and dehydrating. Subsequently, the substance can be reformulated into solution by adding sterile water for injection before clinical use. However, the dose of tetrodotoxin for pharmaceutical use is in the range of 0.5~60 μg, which is so low that a solid residue cannot be generated from a solution of tetrodotoxin after freeze drying and dehydrating. Therefore, it is necessary to add pharmaceutically acceptable excipient (s) so as to provide a framework for such a trace amount of tetrodotoxin to attach to, and enabling the generation of solid residue after freeze drying and dehydrating. However, neither citrate which is used in the scientific tool drug of tetrodotoxin, or mannitol, the most popular excipient, is able to generate acceptable results in our experiments. With a citrate used as excipient, the appearance of the freeze-dried powder shrank and disfigured at 40° C., not meeting the clinical criteria, while the content of tetrodotoxin declined gradually, and the content of related substances became greater than the main peak of the control solution at day 5, exceeding the specified limit and not meeting the clinical criteria either. With only mannitol used as excipient, the appearance of the product met the criteria but the content of tetrodotoxin declined gradually, while the content of related substances became greater than the main peak of the control solution at day 5, exceeding the specified limit and not meeting the clinical criteria (See Table 3).

Storing at 25° C. for six months with only a citrate used as excipient, the content of tetrodotoxin declined to 95.1% from 100% at month zero, a drop of 4.9%, meanwhile the related substances had a relative content greater than the main peak of the control solution, exceeding the specified limit and not meeting the criteria. With mannitol used as excipient, the content of tetrodotoxin declined to 96.59% at month 6 from 100% of month 0, a drop of 3.41%, meanwhile the related substances had a relative content greater than the main peak of the control solution, exceeding the specified limit and not meeting the criteria (See Table 4).

TABLE 3

| | Formulation | | | |
|---|---|---|---|---|
| | Citrate | | Mannitol | |
| | Appearance | | | |
| Content and | Slack white cake-shaped solid. Nearly shrank and disfigured completely after standing for a day at 40° C. The appearance did not meet the criteria. | | Slack white cake-shaped solid. No obvious change was found after standing for 10 days at 40° C. The appearance met the criteria. | |
| related substances | Tetrodotoxin content (%) | Related substance (%) | Tetrodotoxin Content (%) | Related substance (%) |
| Limit | 90-110 | <main peak area of control solution | 90-110 | <main peak area of control solution |
| Day 0 | 100 | <main peak area of control solution | 100 | <main peak area of control solution |
| Day 1 | 98.97 | <main peak area of control solution | 99.86 | <main peak area of control solution |
| Day 3 | 97.26 | <main peak area of control solution | 99 | <main peak area of control solution |
| Day 5 | 96.19 | >main peak area of control solution | 97.69 | >main peak area of control solution |
| Day 10 | 93.18 | >main peak area of control solution | 95.55 | >main peak area of control solution |

TABLE 4

| Content and related substances | Formulation | | | |
|---|---|---|---|---|
| | Citrate | | Mannitol | |
| | Appearance | | | |
| | Slack white cake-shaped solid. Gradually shrank and disfigured into crystal-like substance and attached to the vial walls. Appearance did not meet the criteria. | | Slack white cake-shaped solid. No obvious change was found being stored at room temperature. The appearance met the criteria. | |
| | Tetrodotoxin content (%) | Related substance (%) | Tetrodotoxin content (%) | Related substance (%) |
| Limit | 90-110 | <main peak area of control solution | 90-110 | <main peak area of control solution |
| Month 0 | 100 | <main peak area of control solution | 100 | <main peak area of control solution |
| Month 1 | 98.8 | <main peak area of control solution | 99.69 | <main peak area of control solution |
| Month 2 | 97.2 | <main peak area of control solution | 98.14 | <main peak area of control solution |
| Month 3 | 96.6 | <main peak area of control solution | 98.04 | <main peak area of control solution |
| Month 6 | 95.1 | >main peak area of control solution | 96.59 | >main peak area of control solution |

Note:
The criteria are not met if content of tetrodotoxin is less than 90% or the related substances' content is greater than the main peak of control solution.

These results suggest that excipients in existing formulation techniques help stabilize the physical part only. A search in publications did not yield any finding related to an additive which was capable of improving the chemical stability of a powder formulation containing only trace amount of tetrodotoxin. The inventors came to realize that it was necessary to find out a new approach to improve the stability of tetrodotoxin formulation to temperature by leveraging on the chemical structure of tetrodotoxin.

By learning the nature of the products of tetrodotoxin degradation and understanding the mechanism of degradation of tetrodotoxin in acidic aqueous solution, the present inventors have solved the problem of preventing the degradation of tetrodotoxin in acidic aqueous solution.

The present invention can be applied to tetrodotoxin, per se, and to its derivatives and analogs. "Derivatives" and "analogs" of tetrodotoxin according to this invention are defined in part as in U.S. Pat. No. 6,030,974 (incorporated herein in its entirety by reference) as amino perhydroquinazoline compounds having the molecular formula $C_{11}H_{17}N_3O_8$. Derivatives and analogs of tetrodotoxin according to this invention are further described in U.S. Pat. No. 5,846,975 (incorporated herein in its entirety by reference) as amino hydrogenated quinazolines and derivatives including the substances described from column 3, line 40 to column 6, line 40. Examples of "derivatives and analogs of tetrodotoxin" according to this invention include, but are not limited to, anhydro-tetrodotoxin, tetrodaminotoxin, methoxytetrodotoxin, ethoxytetrodotoxin, deoxytetrodotoxin and tetrodonic acid, 6 epi-tetrodotoxin, 11-deoxytetrodotoxin as well as the hemilactal type TTX analogs (e.g. 4-epi-TTX, 6-epi-TTX, 1'-deoxy-TTX, 4-epi-11-deoxy-TTX, TTX-8-O-hemisuccinate, chiriquitoxin, 11-nor-TTX-6(S)-ol, 1'-nor-TTX-6(R)-ol, 11-nor-TTX-6,6-diol, 11-oxo-TTX and TTX-11-carboxylic acid), the lactone type TTX analogs (e.g. 6-epi-TTX (lactone), 11-deoxy-TTX (lactone), 1'-nor-TTX-6(S)-ol (lactone), 11-nor-TTX-6(R)-ol (lactone), 11-nor-TTX-6,6-diol (lactone), 5-deoxy-TTX, 5,11-dideoxy-TTX, 4-epi-5,11-didroxy-TTX, 1-hydroxy-5,11-dideoxy-TTX, 5,6,11-trideoxy-TTX and 4-epi-5,6,11-trideoxy-TTX) and the 4,9-anhydro type TTX analogs (e.g. 4,9-anhydro-TTX, 4,9-anhydro-6-epi-TTX, 4,9-anhydro-11-deoxy-TTX, 4,9-anhydro-TTX-8-O-hemisuccinate, 4,9-anhydro-TTX-11-O-hemisuccinate). The typical analogs of TTX possess only ⅛ to ¹⁄₄₀ of the toxicity of TTX in mice, based upon bioassay in mice. It has been observed that the analogs produce joint action, and do not interact adversely. "Joint action" may be either additive or synergistic. Examples of TTX analogs include novel TTX analogs isolated from various organisms, as well as those that are partially or totally chemically synthesized (see e.g., Yotsu, M. et al. Agric. Biol. Chem., 53(3): 893-895 (1989)). Analogs of TTX bind to the same site on the alpha subunit of sodium channels as does TTX.

In 1965 T. Goto et al pointed out that acids catalyze epimerization of tetrodotoxin and turn the latter into 4-epi-tetrodotoxin and further to 4,9-dehydro tetrodotoxin (Tetrahedron. 1965. Vol. 21. 2059-2088). In addition, tetrodotoxin refluxed in water, when heated, turns into tetrodonic acid (Annals New York Academy of Sciences. 1985, 479:32-43).

Interconversion Among Tetrodotoxin, 4-epi-tetrodotoxin, 4,9-anhydrotetrodotoxin and Tetrodonic acid:

Tetrodotoxin epimerizes in acidic aqueous solution into 4-epi-tetrodotoxin and 4,9-dehydro tetrodotoxin, thus its content declines. It will turn into tetrodonic acid if heated in reflux.

The aforementioned conclusion is evidenced by the studies on extraction, purification, and structure modification of tetrodotoxin, as well as on determination of 4-epi-tetrodotoxin and 4,9-anhydro tetrodotoxin over a long time.

It is reported that tetrodotoxin turns into 4-epi-tetrodotoxin and 4,9-anhydro tetrodotoxin in acidic aqueous solution. A thermodynamic study was conducted on tetrodotoxin to verify this.

The study proceeded as follows: a number of tetrodotoxin solutions having the same concentration but different pH values were balanced in aqueous solutions at 80° C.±1° C. and 90° C.±1° C., respectively. Then samples were taken at various balancing time points and frozen to −18° C. The degradation products and their contents were determined by HPLC (Zhou et al, U.S. Pat. No. 6,562,968). Results are shown in Tables 5 and 6.

TABLE 5

Thermodynamic Study on Tetrodotoxin at 80° C. (pH 4.67)

| Time (min) | Residue of tetrodotoxin (%) | Degradation products (%) | | | Remarks |
|---|---|---|---|---|---|
| | | 4-epi-tetrodotoxin | 4.9-anhydro tetrodotoxin | Tetrodonic acid | |
| 0 | 100 | 0 | 0 | 0 | |
| 30 | 89.2 | 4.5 | 4.7 | 0 | |
| 60 | 80.4 | 7.4 | 9.3 | 0 | |
| 90 | 75.2 | 9.1 | 13.5 | 0 | |
| 120 | 70.1 | 9.4 | 17.1 | 0 | |
| 240 | 58.9 | 9.4 | 28.1 | 0 | |

As shown in Table 5, tetrodotoxin turned into 4-epi-tetrodotoxin and 4,9-anhydro tetrodotoxin in acidic aqueous solution at 80° C.

TABLE 6

Thermodynamic Study on Tetrodotoxin at 90° C. (pH 4.85)

| Time (min) | Residue of tetrodotoxin (%) | Degradation products (%) | | | Remarks |
|---|---|---|---|---|---|
| | | 4-epi-tetrodotoxin | 4.9-anhydro tetrodotoxin | Tetrodonic acid | |
| 0 | 98.5 | 0.76 | 0.76 | 0 | |
| 30 | 68.8 | 11.9 | 13.9 | 1.7 | |
| 90 | 53.5 | 9.7 | 29.3 | 4.9 | |
| 120 | 50.6 | 8.8 | 32.7 | 6.1 | |
| 240 | 44 | 7.9 | 34.6 | 9.8 | |

As shown in Table 6, tetrodotoxin turned into 4-epi-tetrodotoxin and 4,9-anhydro tetrodotoxin in acidic aqueous solution at 90° C., and partially further into tetrodonic acid.

The common derivatives of Tetrodotoxin
(1) 4-epi-Tetrodotoxin
(2) 4,9-anhydor-Tetrodotoxin
(3) Tetrodonic acid Tetrodotoxin, 4-epi-tetrodotoxin and 4,9-anhydro tetrodotoxin have similar chemical properties. 4-epi-tetrodotoxin shares the same molecular formula and molecular weight with tetrodotoxin but its hydroxyl group on C4 has a different three dimensional position. 4,9-anhydro tetrodotoxin is missing a $H_2O$ in its molecular formula from that of tetrodotoxin and 4-epi-tetrodotoxin, and less 18 in the molecular weight, but they have significant distinction in terms of bioactivity. For example, the toxicity of tetrodotoxin is 4500 mouse units/milligram; 4-epi-tetrodotoxin, 710 mouse units/milligram; 4-epi anhydrotetrodotoxin, only 92 mouse units/milligram (Toxicon. 1985, 23:271~276). Because of such significant differences in bioactivity, tetrodotoxin will lose its medical Value once it is converted into 4-epi-tetrodotoxin or 4,9-dehydro tetrodotoxin and thus its bioactivity will be reduced greatly.

Chemical Mechanism of Tetrodotoxin Degradation

The molecular structure of tetrodotoxin indicates that C-4 is special as it is adjacent to N, connecting an equatorial bonded hydroxyl and an axial bonded proton. Therefore, the C-4 hydroxyl group has special chemical and physiological activity. In the presence of $H^+$ of a solution, $H^+$ interacts with the oxygen atom of the C-4 hydroxyl so that B is inverted from A. If a $H_2O$ molecule is removed from B, a positively charged C is resulted. In a solution where C interacts with a water molecule, E or D will be resulted if the water molecule attacks at the position where the previous $H_2O$ is removed or at the opposite position. If $H^+$ is removed from E, A or the original tetrodotoxin structure is resulted; so it is with D to result in F. The difference between F and A is the interchange of positions between the proton and the hydroxyl: the C-4 proton of A is an axial bond, and the hydroxyl is an equatorial bond; while the C-4 proton of F is equatorial and the hydroxyl is axial. Structures like A and F are called epimers. The mechanism of epimerization is as follows:

Structure A is named "tetrodotoxin", the main content of the extract from puffer fish; F is named 4-epi-tetrodotoxin, which readily results in more stable 4,9-anhydro-tetrodotoxin as a $H_2O$ molecule is easily removed under the interaction of $H^+$ to the adjacent C-4 hydroxyl group and C-9 hydroxyl group. These three types of "fugu toxins" are significantly different in terms of bioactivity but not so different chemically.

Therefore we come to conclude that tetrodotoxin becomes unstable under the interaction of water molecule as a proton causes epimerization and further, 4,9-anhydro-tetrodotoxin is resulted. In order to prevent the epimerization of tetrodotoxin, the C-4 hydroxyl must not be epimerized. Thus the best approach to uphold the stability of tetrodotoxin is to reduce the C-4 hydroxyl. For this purpose, we synthesized 4-deoxy-tetrodotoxin with its structure shown below:

4-deoxy-Tetrodotoxin

4-Deoxy-tetrodotoxin is very stable as it did not change in a water solution after being boiled for 2 hours, as shown by HPLC analysis. However, its $LD_{50}$ is 3336.5 μg/kg, or 330 times less than the toxicity of tetrodotoxin. Its analgesic effect was examined with acetic acid induced writhing in mice, and the results indicated that its effect is approximately 330 times lower than that of tetrodotoxin.

Based upon the experimental results above, we come to the conclusion: the C-4 hydroxyl group of the tetrodotoxin molecule is the center of its bioactivity as it exists to play a key role for that. Meanwhile it is critical to keep it equatorial. What can change it to axial is a water molecule; therefore this becomes the key to how the degradation of tetrodotoxin can be prevented. In order to strengthen the stability of tetrodotoxin when selecting the composition of freeze-dried powder containing a trace amount of tetrodotoxin, it is necessary to identify those additives which keep the C-4 hydroxyl group in an equatorial position.

Mechanism of epimerization of the C-4 hydroxyl of group of tetrodotoxin

A (TTX) ⇌ (+H⁺) B ⇌ (−H₂O) C ⇌ (+H₂O) D + E
D ⇌ (−H⁺) F (4-epi-TTX)
E ⇌ (−H⁺) A (TTX)

As the C-4 hydroxyl group and its three-dimensional position are key to the bioactivity of tetrodotoxin, we use this as the starting point to seek for a pharmaceutically acceptable auxiliary substance which does not cause the C-4 hydroxyl group or its position to change, thereby prevent it from epimerizing. Firstly, the proton of the hydroxyl is prone to forming a hydrogen bond with an electronegative atom like an oxygen atom. There are six electrons in the outer shell of an oxygen atom, leaving two pairs of electrons unused after forming a chemical compound, thus resulting strong electronegativity which enables it to form hydrogen bonds with the proton on the C-4 hydroxyl group and the proton adjacent to the nitrogen atom. Forming of these hydrogen bonds results in a hexatomic ring, thereby "locking" the C-4 hydroxyl, or to say, fixing the three-dimensional position of the C-4 hydroxyl. Secondly, considering the two hexatomic forms in the tetrodotoxin molecule are assembled like two chairs, the possibility is contemplated to find a compound which has a similar structure which enables wrapping of the tetrodotoxin molecule. Compounds meeting with these two requirements are disaccharides and so which contain glucosidic bonds. Based upon above analysis and continuous studies, we have discovered that addition of a certain amount of disaccharide(s) like lactose, sucrose, cellibiose and maltose in the freeze-dried tetrodotoxin powder formulation indeed improves the stability. After storing at room temperature for one year, the contents of tetrodotoxin and related substances did not noticeably change, meeting standard clinical criteria. In the following, lactose is taken as an example to explain the mechanism of preventing the C-4 hydroxyl group from epimerizing through the formation of hydrogen bond between tetrodotoxin and a disaccharide.

A glucosidic bond is also present in ficolls like polyglucose and in dextrans, or analogs like hydroxyethyl starch, hydroxypropyl cyclodextrin, and these compounds have a structure similar to that of tetrodotoxin. By the same theory, they should also be able to stabilize tetrodotoxin. Our studies show ficoll has such action indeed. Those molecules like monosaccharides (glucose, fructose, mannitol) which contain no glucosidic bond cannot "lock" the C-4 hydroxyl, therefore fail to prevent tetrodotoxin from epimerizing. Without being bound by any theory of the invention, the reason could be the interaction between the dipole of the C-1 hydroxyl in β isomer and in parallel, the dipole of the epoxy in the monosaccharide, leads to repulsion. Such dipole-dipole repulsion does not help the epoxy atom forming the hydrogen bond in a hexacyclic ring (Jingyan WANG et al, Biochemistry, Beijing Advanced Education Publishing, 2002.13).

equatorial hydroxy (β isomer)

The dipole of C-1 hydroxyl in the 13 isomer is approximately parallel to the dipole of the epoxy in the monosaccharide.

To overcome the deficiencies in existing technologies, the inventors invented a pharmaceutical formulation of tetrodot- Tetrodotoxin        Lactose Locking C-4 hydroxyl through the formation of hydrogen bond between lactose and tetrodotoxin oxin, a bioactive substance which is not stable in aqueous solution or in the form of freeze dried citrate, and a preparation method thereof. The formulation is freeze-dried and can be stored for a long term at room temperature. Before clinical use, the formulation can be regenerated by adding an aqueous solution adequate for human use, preferably sterile, pyrogen free water suitable for pharmaceutical use, and then administered by injection.

This invention is related to a stable pharmaceutical composition of freeze-dried tetrodotoxin powder containing a trace amount of bioactive ingredient, namely tetrodotoxin, stabilizer(s) and solvent(s), wherein said tetrodotoxin has an amount of 0.5-60 µg per dose, with remaining amounts being stabilizer(s) and solvent(s).

The aforementioned tetrodotoxin includes tetrodotoxin or its analogs like anhydrotetrodotoxin, amino-tetrodtoxin, methoxytetrodotoxin and ethoxytetrodotoxin. The bioactive tetrodotoxin is extracted from the ovaries and livers of puffer fish, a marine animal; or from other species like amphibian, turbellaria, nemertean, steroidea, sagitta, and gastropoda; or from some bacteria like *vibrio alginolyticus*. The extraction can be done by the method disclosed in existing publications, such as Zhou, et al., U.S. Pat. No. 6,552,191. The analogs thereof can be compounds obtained by modifying the structure of tetrodotoxin.

In this invention, tetrodotoxin as the bioactive substance for safe use by injection in humans has an amount in each dose ranging from 0.5 µg to 60 µg, of which alone a freeze-dried formulation cannot be made. Therefore, pharmaceutically acceptable excipient(s) should be added so as to increase the concentration of solutes in a solution before being freeze dried. Our studies show that tetrodotoxin during storage can only be kept from epimerizing to 4-epi-tetrodotoxin and 4,9-dehydro tetrodotoxin when one or more stabilizing substances are added. In this invention, such substances are lactose, sucrose, maltose; ficoll, including polyglucose, dextran; or analogues thereof, including hydroxyethyl starch, hydroxypropyl cyclodextrin, in the range of 5-500 mg per dose, preferably 5-200 mg per dose, more preferably 10-100 mg per dose.

The bioactive tetrodotoxin in this invention is hardly soluble in water, thus it is necessary to add a solvent to help tetrodotoxin dissolve and obtain required concentration. Tetrodotoxin's structure suggests that it is an organic base, therefore soluble in acids. However, strong acids will decompose it, so non-volatile organic acids like citric acid, tartaric acid, malic acid or lactobionic acid are preferable as such an acid can form an organic salt with tetrodotoxin and dissolve in water, meanwhile make it easy to control the acidity. Experimental results suggest that the amount of solvent(s) used in this invention should range from 0.00005 to 0.0050 mg per dose, preferably from 0.00005 to 0.0010 mg per dose, more preferably 0.00010 to 0.0010 mg per dose, more preferably 0.00010 to 0,001 mg per dose, and keep the pH of the solution before freeze-drying in the range of 3.0~6.0.

This invention relates to obtaining a solid form by freeze-drying an aqueous solution of, or a solution of water soluble solvent with, the bioactive tetrodotoxin and a disaccharide or a polyglucose or an analogue thereof (e.g. a disaccharide or polyglucose as described in Remington's Pharmaceutical Sciences, Seventeenth Edition. 1985, 1314 ff.). The said aqueous solution can be readily prepared. Bacteria and other small contaminants can be removed by micro-filtration, e.g. through a 0.22 µm membrane. The solution can then be ultrafiltered through a 10,000 molecular weight cutoff ultrafilter. The solution is then freeze dried to obtain a sterile and pyrogen-free powder, which is stable and the bioactive tetrodotoxin is stable for a long time.

In order to obtain a constant and adequate pH for the freeze-dried powder and to prevent irritation to the local tissue or necrosis, a certain amount of solvent(s) is added to control the pH in the range of 3.0 to 6.0. If the pH is lower than 3.0, adjust it with diluted sodium (potassium) hydroxide or other pharmaceutically acceptable salt, of which the amount is based upon the pH of the solution before freeze-drying.

The freeze-dried tetrodotoxin formulation of this invention may typically be prepared by the following steps: dissolve the solvents and stabilizers separately, and dissolve tetrodotoxin in the solvents, merge with the stabilizer solution, add water for injection to specified volume, check the pH to be in the range of 3.0-6.0; otherwise adjust it with sodium (potassium) hydroxide or corresponding a sodium (potassium) salt of an organic acid, eliminate bacteria, filter and ultra-filter, fill in vials, loosely place stoppers, freeze dry, put stoppers in place. Covers describing the pharmaceutical product are then rolled onto the vials.

The aforementioned freeze-dried composition can be regenerated by adding aqueous solution suitable for human use so as to obtain a transparent liquid which is sterile and pyrogen-free, and ready for intramuscular or subcutaneous injection. Said aqueous solution is sterile water for injection or other aqueous solution typically has a volume of 0.5-5 mL, preferably 1-2 mL.

The manufacturing process consists of the following step:
1. Dissolve a certain amount of solvent in water for injection.
2. Dissolve a pH-adjusting substance in water for injection.
3. Dissolve a disaccharide or polyglucose or an analogue thereof as a stabilizer in water for injection.
4. Add a calculated amount of solvent solution in a trace amount of tetrodotoxin, stir and dissolve.
5. Add 4 into 3, and add water for injection to specified volume, shake well.
6. Examine the pH of the solution to be in the range of 3.0-6.0; otherwise, adjust it with the pH-adjusting solution.
7. Sterilize by filtering (e.g. with Millipore filtering system) and ultrafiltering (e.g. with Pall ultrafiltering system) to obtain a sterile and pyrogen-free transparent solution,
8. Dispatch the resulting solution in 7 in vials with specified amount in each vial, put on covers loosely and place into a freeze dryer. Refrigerate until the surface temperature declines to under −40° C., then freeze further to under −50° C. Switch on the vacuum pump, maintain the pressure under 5 Pa, and allow the temperature rise without intervention to the specified level. Allow standing for 24 hours, then escalate the temperature to 30° C. for a period of 10 hours. Close the stoppers automatically.
9. Take out the vials and roll on covers.

Comparing with existing technologies, this invention has pertinent and significant advantages as follows:

It is difficult to store tetrodotoxin injection in refrigeration (4-8° C.) or at room temperature. Epimerization readily occur at room temperature to turn tetrodotoxin into 4-epi-tetrodotoxin and 4, 9 anhydro-tetrodotoxin, losing the pharmaceutical effect. The inventors performed extensive studies to find the stabilizer(s) which prevent tetrodotoxin from epimerizing, thereby to keep the trace amount of tetrodotoxin stable in the formulation at room temperature. Particularly:

1. Stablilizer(s) like a disaccharide or a polyglucose or an analogue thereof is added in the formulation to effectively prevent tetrodotoxin from epimerizing during storage, i.e. prevent tetrodotoxin from turning into 4-epi-tetrodotoxin and 4, 9 anhydro-tetrodotoxin, thereby to ensure product quality.
2. Freeze drying technique is adopted to improve the stability of the product as there is little water left.
3. The combination of the above techniques can effectively solve the stability problem for trace amount of tetrodotoxin in pharmaceutical formulations.
4. It is not required to store the drug product at 4-8° C. by refrigeration but at room temperature, therefore a large portion of storage and transportation costs can be saved and clinical use of the product is made convenient. More importantly, this invention enables a safe and reliable product with stable quality and storage duration for one year or more.

EXAMPLES

Example 1

Freeze dried formulations of tetrodotoxin and a disaccharide (lactose, sucrose, maltose and ficoll) were prepared with the amounts as specified in Table 7. Fructose (monosaccharide) was used as excipient in Formulation 1, whereas disaccharides were used as stabilizer (and excipient simultaneously) in Formulations 2, 3, 4 and 5. Citric acid (solvent) and the stabilizer were dissolved separately in water for injection; then tetrodotoxin was dissolved in the citric acid solution, followed by the addition of the stabilizer solution. Next, water for injection was added till the specified volume. The resulting solution was stirred evenly, and its pH was adjusted to 4.0; then bacteria were removed by filtering and ultrafiltering. The resulting solution was filled in glass vials to specified volume; then covers were put on loosely, and the vials were put in a freeze dryer. After the temperature of the vials was reduced to −40° C., the freeze chamber was switched on to further reduce the temperature to under −50° C. The vacuum pump was started to maintain the pressure under 5 Pa; then the temperature was allowed to rise without intervention to a specified level. After vials being allowed standing for 24 hours, the temperature was escalated naturally to 30° C. for a period of at least 10 hours. The stoppers were closed tightly and covers were rolled on to finish.

TABLE 7

| | (100 doses) | | | | |
|---|---|---|---|---|---|
| | Formulation | | | | |
| | 1 | 2 | 3 | 4 | 5 |
| Tetrodotoxin | 3 mg | 3 mg | 3 mg | 3 mg | 3 mg |
| Fructose | 3000 mg | — | — | — | — |
| Lactose | — | 3000 mg | — | — | — |
| Sucrose | — | — | 3000 mg | — | — |
| Maltose | — | — | — | 3000 mg | — |
| Ficoll | — | — | — | — | 3000 mg |
| Citric acid | 0.012 mg | 0.012 mg | 0.012 mg | 0.012 mg | 0.012 mg |
| Water for injection | add to 100 ml | | | | |

Stability tests were performed on the above freeze dried formulations and tetrodotoxin injection (liquid form) at 40° C. simultaneously. Samples were taken on day 1, 3, 5, and 10. Contents of tetrodotoxin and related substances were detected by HPLC, and compared with day 0. Results were presented in Table 8.

TABLE 8

Results of Stability Studies at 40° C. on Tetrodotoxin Injection (liquid form) and Various Freeze Dried Tetrodotoxin Formulations

| | Formulations | | | | | | | | | | |
|---|---|---|---|---|---|---|---|---|---|---|---|
| | 1 | | 2 | | 3 | | 4 | | 5 | | 6* |
| | Appearance | | | | | | | | | | |
| Content and related substances | No crystal or powder was formed. The appearance did not meet the criteria. | | Slack white cake-shaped solid. No obvious change was found after standing for 10 days at 40° C. The appearance met the criteria. | | Slack white cake-shaped solid. No obvious change was found after standing for 10 days at 40° C. The appearance met the criteria. | | Slack white cake-shaped solid. No obvious change was found after standing for 10 days at 40° C. The appearance met the criteria. | | Slack white cake-shaped solid. No obvious change was found after standing for 10 days at 40° C. The appearance met the criteria. | | Colorless, transparent liquid. No obvious change was found after standing for 10 days at 40° C. |
| | Content (%) | Related Substances (%) | Content (%) | Related Substances (%) | Content (%) | Related Substances (%) | Content (%) | Related Substances (%) | Content (%) | Related Substances (%) | Content (%) | Related Substances (%) |
| Lmit | 90-110 | <main peak area of control solution | 90-110 | <main peak area of control solution | 90-110 | <main peak area of control solution | 90-110 | <main peak area of control solution | 90-110 | <main peak area of control solution | 90-110 | <main peak area of control solution |

TABLE 8-continued

Results of Stability Studies at 40° C. on Tetrodotoxin Injection (liquid form) and Various Freeze Dried Tetrodotoxin Formulations

| | Formulations | | | | | |
|---|---|---|---|---|---|---|
| | 1 | 2 | 3 | 4 | 5 | 6* |
| | Appearance | | | | | |
| Content and related sub-stances | No crystal or powder was formed. The appearance did not meet the criteria. | Slack white cake-shaped solid. No obvious change was found after standing for 10 days at 40° C. The appearance met the criteria. | Slack white cake-shaped solid. No obvious change was found after standing for 10 days at 40° C. The appearance met the criteria. | Slack white cake-shaped solid. No obvious change was found after standing for 10 days at 40° C. The appearance met the criteria. | Slack white cake-shaped solid. No obvious change was found after standing for 10 days at 40° C. The appearance met the criteria. | Colorless, transparent liquid. No obvious change was found after standing for 10 days at 40° C. |
| | Content (%) | Related Sub-stances (%) | Content (%) | Related Substances (%) | Content (%) | Related Substances (%) | Content (%) | Related Substances (%) | Content (%) | Related Substances (%) | Content (%) | Related Substances (%) |
| Day 0 | 100 | <main peak area of control solution | 100 | <main peak area of control solution | 100 | <main peak area of control solution | 100 | <main peak area of control solution | 100 | <main peak area of control solution | 100 | <main peak area of control solution |
| Day 1 | 99.7 | <main peak area of control solution | 100 | <main peak area of control solution | 99.46 | <main peak area of control solution | 99.55 | <main peak area of control solution | 99.47 | <main peak area of control solution | 98.53 | <main peak area of control solution |
| Day 3 | 99.06 | <main peak area of control solution | 99.72 | <main peak area of control solution | 99.24 | <main peak area of control solution | 99.21 | <main peak area of control solution | 99.61 | >main peak area of control solution | 96.66 | <main peak area of control solution |
| Day 5 | 97.54 | >main peak area of control solution | 99.73 | <main peak area of control solution | 99.77 | <main peak area of control solution | 99.69 | <main peak area of control solution | 99.72 | <main peak area of control solution | 92.73 | >main peak area of control solution |
| Day 10 | 95.99 | >main peak area of control solution | 99.97 | <main peak area of control solution | 99.56 | <main peak area of control solution | 99.18 | <main peak area of control solution | 99.75 | <main peak area of control solution | 90.06 | >main peak area of control solution |

Notes:
1. 6* is tetrodotoxin injection (liquid form)
2. The criteria are not met if content of tetrodotoxin is less than 90% or the related substances' content is greater than the main peak of control solution; then the product cannot be used as a medicine.

Fructose was used as excipient in Formulation 1, of which the appearance did not meet the criteria. At 40° C. test, the content of tetrodotoxin in this formulation declined gradually from 100% in day 0 to 95.99% in day 10, or a decrease of 4.01%. On the other hand, the content area of related substances exceeded the major peak area of the control solution, not meeting the criteria. Therefore fructose is unable to prevent tetrodotoxin from epimerizing, not helpful for the stability of tetrodotoxin.

Disaccharides, lactose, sucrose, maltose and ficoll, were used as the stabilizer in formulations 2, 3, 4 and 5, respectively. At 40° C. standing for 10 days, these formulations did not show significant changes in the contents of tetrodotoxin or related substances. The contents of tetrodotoxin were 99.97%, 99.56%, 99.18%, and 99.75%, respectively, while the content areas of related substances were all smaller than the major area of the control solution. These results indicate that these formulations having greatly improved stability meet the criteria for medicines, and disaccharides are capable of preventing tetrodotoxin from epimerizing and thus can protect the latter. Formulation 6 is the liquid form of tetrodotoxin injection, which under the same test conditions had a gradually declining content of tetrodotoxin from 100% of day 0 to 90.06% of day 10, or a decrease of 9.94%, whereas the content area of related substances exceeded the major peak area of the control solution from day 3 on, not meeting the criteria. Therefore, these results suggest that freeze dried tetrodotoxin formulations with disaccharides as stabilizers have a higher stability than the liquid form of tetrodotoxin injection.

A long term stability study was performed at room temperature on the above freeze dried tetrodotoxin formulations and the liquid form of tetrodotoxin injection, with samples taken in month 1, 2, 3, 6, 9 and 12. Contents of tetrodotoxin and related substances were detected by HPLC, and compared with day 0. Results were presented in Table 9.

TABLE 9

Results of Stability Studies at Room Temperature on Tetrodotoxin Injection (liquid form) and Various Freeze Dried Tetrodotoxin Formulations

| Content and related substances | Formulations | | | | | | | | | | | |
|---|---|---|---|---|---|---|---|---|---|---|---|---|
| | 1 | | 2 | | 3 | | 4 | | 5 | | 6* | |
| | Appearance | | | | | | | | | | | |
| | No crystal or powder was formed. The appearance did not meet the criteria. | | Slack white cake-shaped solid. No obvious change was found after standing at room temperature. The appearance met the criteria. | | Slack white cake-shaped solid. No obvious change was found after standing for at room temperature. The appearance met the criteria. | | Slack white cake-shaped solid. No obvious change was found after standing for at room temperature. The appearance met the criteria. | | Slack white cake-shaped solid. No obvious change was found after standing for at room temperature. The appearance met the criteria. | | Colorless, transparent liquid. No obvious change was found after standing at room temperature. | |
| | Content (%) | Related Sub-stances (%) | Content (%) | Related Substances (%) | Content (%) | Related Substances (%) | Content (%) | Related Substances (%) | Content (%) | Related Substances (%) | Content (%) | Related Sub-stances (%) |
| Limit | 90-110 | <main peak area of control solution | 90-110 | <main peak area of control solution | 90-110 | <main peak area of control solution | 90-110 | <main peak area of control solution | 90-110 | <main peak area of control solution | 90-110 | <main peak area of control solution |
| Month 0 | 100 | <main peak area of control solution | 100 | <main peak area of control solution | 100 | <main peak area of control solution | 100 | <main peak area of control solution | 100 | <main peak area of control solution | 100 | <main peak area of control solution |
| Month 1 | 97.53 | <main peak area of control solution | 100.07 | <main peak area of control solution | 99.78 | <main peak area of control solution | 100.48 | <main peak area of control solution | 99.97 | <main peak area of control solution | 95.34 | <main peak area of control solution |
| Month 2 | 94.16 | >main peak area of control solution | 100.08 | <main peak area of control solution | 99.5 | <main peak area of control solution | 100.07 | <main peak area of control solution | 99.86 | <main peak area of control solution | 92.58 | >main peak area of control solution |
| Month 3 | 92.09 | >main peak area of control solution | 100.1 | <main peak area of control solution | 100.79 | <main peak area of control solution | 99.83 | <main peak area of control solution | 100.68 | <main peak area of control solution | 89.07 | >main peak area of control solution |
| Month 6 | 90.52 | >main peak area of control solution | 100.13 | <main peak area of control solution | 99.53 | <main peak area of control solution | 100.3 | <main peak area of control solution | 99.29 | <main peak area of control solution | 82.25 | >main peak area of control solution |
| Month 9 | 86.27 | >main peak area of control solution | 100.04 | <main peak area of control solution | 100.2 | <main peak area of control solution | 99.65 | <main peak area of control solution | 99.32 | <main peak area of control solution | 77.06 | >main peak area of control solution |
| Month 12 | 83.19 | >main peak area of control solution | 101.92 | <main peak area of control solution | 99.89 | <main peak area of control solution | 99.87 | <main peak area of control solution | 99.47 | <main peak area of control solution | 73.38 | >main peak area of control solution |

Notes:
1. 6* is tetrodotoxin injection (liquid form)
2. The criteria are not met if content of tetrodotoxin is less than 90% or the related substances' content is greater than the main peak of control solution; then the product cannot be used as a medicine.

Fructose was used as the excipient in Formulation 1, the appearance of which did not meet the criteria. During the storage period, the tetrodotoxin content declined from 100% in month 0 to 83.19% in month 12, or a drop of 16.81%. In month 2, the content of related substances exceeded the major peak area of the control solution, not meeting the criteria and not qualified for clinical use. Disaccharides, lactose, sucrose, maltose and ficol, were used as stabilizer in formulations 2, 3, 4 and 5, respectively. At room temperature standing for 12 months, these formulations did not turn out significant changes in appearance, content of tetrodotoxin or related substances. The contents of tetrodotoxin were 101.92%, 99.89%, 99.87%, and 99.47%, respectively, while the content areas of related substances were all smaller than the major area of the control solution, meeting the criteria for clinical use. Formulation 6 is the liquid form of tetrodotoxin injection, which under the same storage conditions had a content of tetrodotoxin declining from 100% in month 0 to 73.38% in month 12, a drop of 26.62%. Since month 2, its content area of related substances had exceeded the major peak area of the control solution, not meeting the criteria and indicating a poor stability. Therefore, disaccharides are capable of protecting trace amount of tetrodotoxin so well that the contents of tetrodotoxin and related substances meet the requirements for clinical use even after 12 months of storage at room temperature. Hence, the stability of tetrodotoxin formulations is maintained.

Example 2

Preparation of Freeze-Dried Powder Formulation Containing the Bioactive Tetrodotoxin 30 μg and Dextran 30 mg The method described in Example 1 was followed to obtain a slack white cake-shaped solid by freezing dry a solution of 0.003% tetrodotoxin and 3% dextran, pH 3.0. Then its stability at 40° C. was studied with samples taken on day 1, 3, 5, 10; the content of tetrodotoxin and related substances were detected by HPLC, and compared to the results of day 0, as shown in Table 10.

TABLE 10

Appearance
Slack white cake-shaped solid. No obvious change was observed after standing for 10 days at 40° C., thus the appearance met with the criteria.

| Contents | Tetrodotoxin (%) | Related substances (%) |
|---|---|---|
| Limit | 90-110 | <main peak area of control solution |
| Day 0 | 100 | <main peak area of control solution |
| Day 1 | 99.46 | <main peak area of control solution |
| Day 5 | 98.63 | <main peak area of control solution |
| Day 10 | 98.13 | <main peak area of control solution |
| Conclusion | | Met medicinal criteria |

The results support that dextran stabilizes tetrodotoxin in this formulation as it has a chemical structure similar to disaccharides. At the high temperature of 40° C., the appearance, contents of tetrodotoxin and related substances meet medicinal standards.

Example 3

Preparation of Freeze-Dried Powder Formulation Containing the Bioactive Tetrodotoxin 60 μg and Lactose 5 mg (or Sucrose, Maltose, Cellobiose)

The method described in Example 1 was followed to obtain a slack white cake-shaped solid by freezing dry a solution of 0.006% tetrodotoxin and 0.5% lactose, pH 4.0. Resulted from this formulation by dissolving in water for injection or pharmaceutically acceptable aqueous solution, a sterile and pyrogen-free transparent solution can be directly used for intramuscular or subcutaneous injection.

Example 4

Preparation of Freeze-Dried Powder Formulation Containing the Bioactive Tetrodotoxin 0.5 μg and Lactose 100 mg (or Sucrose, Maltose, Cellobiose)

The method described in Example 1 was followed to obtain a slack white cake-shaped solid by freezing dry a solution of 0.00005% tetrodotoxin and 10% lactose, pH 6.0. After being dissolved in aqueous solution, the resultant solution can be directly used for intramuscular or subcutaneous injection.

Example 5

Preparation of Freeze-Dried Powder Formulation Containing the Bioactive Tetrodotoxin 5 μg, Lactose 15 mg and Sucrose 15 mg (or Maltose, Cellobiose)

The method described in Example 1 was followed to obtain a slack white cake-shaped solid by freezing dry a solution of 0.0005% tetrodotoxin, 1.5% lactose and 1.5% sucrose, pH 4.5. Resulted from this formulation by dissolving in water for injection or pharmaceutically acceptable aqueous solution, a sterile and pyrogen-free transparent solution can be directly used for intramuscular or subcutaneous injection.

Example 6

Preparation of Freeze-Dried Powder Formulation Containing the Bioactive Tetrodotoxin 20 μg, Lactose 15 mg (or Sucrose, Maltose, Cellobiose) and Mannitol 15 mg The method described in Example 1 was followed to obtain a slack white cake-shaped solid by freezing dry a solution of 0.002% tetrodotoxin, 1.5% lactose and 1.5% mannitol, pH 5.5. Resulted from this formulation by dissolving in water for injection or pharmaceutically acceptable aqueous solution, a sterile and pyrogen-free transparent solution can be directly used for intramuscular or subcutaneous injection.

The samples obtained through this method had a tetrodotoxin content of 99.65% after being stored for one year at room temperature, and its content of related substances was smaller than the major peak area of the control solution, meeting the requirements for clinical use, whereas using mannitol alone failed to achieve this objective. Therefore this substantiates the significant preserving action by lactose or sucrose, maltose, cellobiose in this freeze-dried formulation.

What is claimed is:

1. A freeze-dried pharmaceutical composition comprising tetrodotoxin or an analog or derivative thereof, at least one stabilizer selected from the group consisting of a disaccharide, a ficoll, a polyglucose, a dextran, hydroxyethyl starch, hydroxypropyl cyclodextrin or analogues thereof; and a pharmaceutically acceptable excipient.

2. The composition of claim 1, wherein said tetrodotoxin, or an analog or derivative thereof is selected from the group consisting of anhydrotetrodotoxin, amino-tetrodotoxin, methoxytetrodotoxin, and ethoxytetrodotoxin.

3. The composition of claim 1, wherein said pharmaceutically acceptable excipient differs from the at least one stabilizer.

4. The composition of claim 3, wherein said pharmaceutically acceptable excipient is mannitol.

5. The composition of claim 1, comprising tetrodotoxin in an amount from about 0.5 to about 60 μg per dose.

6. The composition of claim 1, wherein the composition further comprises a solvent residue.

7. The composition of claim 1, comprising a non-volatile organic acid.

8. The composition of claim 7, wherein the non-volatile organic acid is selected from the group consisting of citric acid, tartaric acid, malic acid and lactobionic acid.

9. The composition of claim 8, wherein the non-volatile organic acid is present in an amount from 0.00005 to 0.0050 mg per dose.

10. The composition of claim 1, wherein the composition has a pH of about 3.0 to about 6.0.

11. The composition of claim 1, wherein the stabilizer is present in the composition in an amount from 5 to 500 mg per dose.

12. The composition of claim 11, wherein the pharmaceutically acceptable excipient differs from the stabilizer, and the excipient and the stabilizer are present in equal amounts.

13. The composition of claim 1, wherein the composition, upon reconstitution with a pharmaceutically acceptable aqueous solution, results in a solution which is suitable for administration to humans.

14. The solution of claim 13, wherein the solution is suitable for administration of a single dose of tetrodotoxin.

15. A method for preparing a freeze-dried composition which, upon reconstitution with a pharmaceutically acceptable aqueous solution, contains one or more doses of tetrodotoxin, comprising the steps of (a) preparing a solution comprising tetrodotoxin, at least one stabilizer, a pharmaceutically acceptable excipient, wherein the solution has a pH in the range from about 3.0 to about 6.0 and wherein the stabilizer is selected from the group consisting of a disaccharide, a ficoll, a polyglucose, a dextran, hydroxyethyl starch, hydroxypropyl cyclodextrin, or analogues thereof, and (b) freeze-drying the solution.

16. The method of claim 15, wherein said tetrodotoxin, or an analog or derivative thereof is selected from the group consisting of anhydrotetrodotoxin, amino-tetrodotoxin, methoxytetrodotoxin, and ethoxytetrodotoxin.

17. The method of claim 15, wherein said pharmaceutically acceptable excipient differs from the at least one stabilizer.

18. The method of claim 17, wherein said pharmaceutically acceptable excipient is mannitol.

19. The method of claim 18, wherein pharmaceutically acceptable solution contains a non-volatile organic acid.

20. The method of claim 19, wherein the non-volatile organic acid is selected from the group consisting of citric acid, tartaric acid, malic acid and lactobionic acid.

21. The composition prepared by the method of claim 15.

22. The composition prepared by the method of claim 18.

23. The composition prepared by the method of claim 20.

24. An injectable solution prepared by a process comprising (a) providing a solution which has a pH in the range from about 3.0 to about 6.0 and contains one or more doses of tetrodotoxin, or an analogue or derivative thereof, at least one stabilizer, wherein the stabilizer is selected from the group consisting of a disaccharide, a ficoll, a polyglucose, a dextran, hydroxyethyl starch, hydroxypropyl cyclodextrin, or analogues thereof; and a pharmaceutically acceptable excipient, (b) freeze-drying the solution; and (c) reconstituting the resulting composition using a pharmaceutically acceptable aqueous solution suitable for injection, wherein the resulting injectable solution retains said one or more doses of tetrodotoxin.

25. The injectable solution according to claim 24, wherein said tetrodotoxin, or an analog or derivative thereof is selected from the group consisting of anhydrotetrodotoxin, amino-tetrodotoxin, methoxytetrodotoxin, and ethoxytetrodotoxin.

26. The injectable solution according to claim 24, wherein said pharmaceutically acceptable excipient differs from the at least one stabilizer.

27. The injectable solution according to claim 26, wherein said pharmaceutically acceptable excipient is mannitol.

28. The injectable solution according to claim 24, wherein the pharmaceutically acceptable aqueous solution is saline.

29. The injectable solution according to claim 24, wherein the amount of tetrodotoxin in the solution is 0.5 to 60 µg.

30. The injectable solution according to claim 24, wherein the solution further comprises a non-volatile organic acid.

31. The injectable solution of claim 30, wherein the non-volatile organic acid is selected from the group consisting of citric acid, tartaric acid, malic acid and lactobionic acid.

32. The injectable solution of claim 31, wherein the non-volatile organic acid is present in an amount from 0.00005 to 0.0050 mg per dose.

33. The injectable solution of claim 24, wherein the stabilizer is present in the composition in the amount of 5-500 mg per dose of tetrodotoxin.

34. The injectable solution of claim 33, wherein the pharmaceutically acceptable excipient differs from the stabilizer, and the excipient and the stabilizer are present in equal amounts.

35. The injectable solution of claim 24, wherein the reconstituted aqueous solution formed is suitable for administration of a single dose.

36. The injectable solution of claim 24, wherein the amount of tetrodotoxin in the reconstituted solution is at least 98% of the amount of tetrodotoxin in the solution prior to the freeze drying.

37. The injectable solution of claim 24, wherein the amount of tetrodotoxin in the reconstituted solution is at least 90% of the amount of tetrodotoxin in the solution prior to the freeze drying.

38. A method for preparing a freeze-dried composition which, upon reconstitution with a pharmaceutically acceptable aqueous solution, contains one or more doses of tetrodotoxin, or an analogue or derivative thereof, comprising the steps of (a) preparing a solution comprising said tetrodotoxin, or analogue or derivative thereof, at least one stabilizer, wherein the stabilizer is selected from the group consisting of a disaccharide, a ficoll, a polyglucose, a dextran, hydroxyethyl starch, hydroxypropyl cyclodextrin, or analogues thereof, a pharmaceutically acceptable excipient and optionally a solvent, wherein the solution has a pH in the range from about 3.0 to about 6.0; (b) freeze-drying the solution.

39. The method of claim 38, wherein said tetrodotoxin, or an analog or derivative thereof is selected from the group consisting of anhydrotetrodotoxin, amino-tetrodotoxin, methoxytetrodotoxin, and ethoxytetrodotoxin.

40. The method of claim 38, wherein said pharmaceutically acceptable excipient differs from the at least one stabilizer.

41. The method of claim 40, wherein said pharmaceutically acceptable excipient is mannitol.

42. The method of claim 38, wherein the amount of the tetrodotoxin in the solution is 0.5 to 60 µg.

43. The method according to claim 42, wherein the solvent is a non-volatile organic acid and is selected from the group consisting of citric acid, tartaric acid, malic acid and lactobionic acid.

44. The method according to claim 43, wherein the non-volatile organic acid is present in an amount from 0.00005 to 0.0050 mg per dose.

45. The method according to claim 38, wherein the stabilizer is present in the composition in the amount of 5-500 mg per dose of tetrodotoxin.

46. The method according to claim 38, wherein the pharmaceutically acceptable excipient differs from the stabilizer, and the excipient and the stabilizer are present in equal amounts.

47. The method according to claim 38, wherein the reconstituted aqueous solution formed is suitable for administration of a single dose.

48. The method according to claim 38, wherein the amount of tetrodotoxin in the reconstituted solution is at least 98% of the amount of tetrodotoxin in the solution prior to the freeze drying.

49. The method according to claim 38, wherein the amount of tetrodotoxin in the reconstituted solution is at least 90% of the amount of tetrodotoxin in the solution prior to the freeze drying.

* * * * *